US009487452B2

(12) United States Patent
Ledoux

(10) Patent No.: US 9,487,452 B2
(45) Date of Patent: Nov. 8, 2016

(54) UREA PASSIVATION TECHNIQUE AND NEW PRODUCT PASSIVATED UREA, TO MAKE UREA OR UREA-BASED COMPOUND UNIVERSALLY BLENDABLE

(71) Applicant: Yara International ASA, Oslo (NO)

(72) Inventor: Francois Ledoux, Cormeilles en Parisis (FR)

(73) Assignee: YARA INTERNATIONAL ASA, Oslo (NO)

(*) Notice: Subject to any disclaimer, the term of this patent is extended or adjusted under 35 U.S.C. 154(b) by 0 days.

(21) Appl. No.: 14/422,937

(22) PCT Filed: Aug. 28, 2013

(86) PCT No.: PCT/EP2013/067799
§ 371 (c)(1),
(2) Date: Feb. 20, 2015

(87) PCT Pub. No.: WO2014/033160
PCT Pub. Date: Mar. 6, 2014

(65) Prior Publication Data

US 2015/0210604 A1 Jul. 30, 2015

(30) Foreign Application Priority Data

Aug. 29, 2012 (NO) .................................... 20120973

(51) Int. Cl.

| | |
|---|---|
| ***C05C 9/00*** | (2006.01) |
| ***C05C 1/00*** | (2006.01) |
| ***C05C 5/00*** | (2006.01) |
| ***C05C 5/04*** | (2006.01) |
| ***C05B 1/02*** | (2006.01) |
| ***C05G 3/00*** | (2006.01) |
| *C07C 273/14* | (2006.01) |

(52) U.S. Cl.
CPC ............... *C05G 3/0041* (2013.01); *C05B 1/02* (2013.01); *C05C 1/00* (2013.01); *C05C 9/00* (2013.01); *C05C 9/005* (2013.01); *C05G 3/0088* (2013.01); *C07C 273/14* (2013.01)

(58) Field of Classification Search
CPC ............. C05C 1/00; C05C 5/04; C05C 5/00; C05B 1/02
See application file for complete search history.

(56) References Cited

U.S. PATENT DOCUMENTS

| | | | |
|---|---|---|---|
| 3,392,007 A | 7/1968 | Christoffel et al. | |
| 3,419,379 A | 12/1968 | Goodale et al. | |
| 4,026,696 A * | 5/1977 | Young | C05C 1/00 423/396 |
| 2010/0031719 A1* | 2/2010 | Hero | C05C 1/02 71/30 |

FOREIGN PATENT DOCUMENTS

| | | |
|---|---|---|
| FR | 2 686 861 | 8/1993 |
| WO | 93/10062 | 5/1993 |
| WO | 99/15480 | 4/1999 |
| WO | 00/07938 | 2/2000 |
| WO | 04/000759 | 12/2003 |
| WO | 2012/064730 | 5/2012 |

OTHER PUBLICATIONS

International Search Report and the Written Opinion of the International Searching Authority issued Feb. 25, 2014 in International (PCT) Application No. PCT/EP2013/067799.

Written Opinion of the International Preliminary Examining Authority issued Sep. 8, 2014 in International (PCT) Application No. PCT/EP2013/067799.

International Preliminary Report on Patentability issued Dec. 4, 2014 in International (PCT) Application No. PCT/EP2013/067799, together with Applicants' replies of Nov. 10, 2014 and Jun. 25, 2014.

Guidance for the Compatibility of Fertilizer Blending Materials, European Fertilizer Manufacturers Association (EFMA), Jun. 2006, pp. 1-12.

* cited by examiner

*Primary Examiner* — Wayne Langel
(74) *Attorney, Agent, or Firm* — Wenderoth, Lind & Ponack, L.L.P.

(57) ABSTRACT

The invention concerns a method of producing passivated urea or urea based compounds for fertilizer blends wherein the urea particles are treated with a mineral acid that reacts with urea and creates a grasping layer. Thereafter a solid base in powder form is added in excess to the particles to coat the acidified particle surface. The invention also concerns a fertilizer blend comprising the passivated urea or urea based compounds with one or more of AN or AN-based compound, NS products, superphosphates, and more generally with a priori most compounds that urea is susceptible to react with when in direct contact. A safe blend comprises more than 40 weight % of the passivated urea.

16 Claims, No Drawings

UREA PASSIVATION TECHNIQUE AND NEW PRODUCT PASSIVATED UREA, TO MAKE UREA OR UREA-BASED COMPOUND UNIVERSALLY BLENDABLE

FIELD OF THE INVENTION

The present invention concerns urea and urea based compounds, and their use in nitrogenous fertilizers.

BACKGROUND

Urea is today the main nitrogenous fertilizer used worldwide. Urea that is chemically pure has a nitrogen content of 46.6% N (expressed as N). Urea that is commonly available and used as fertilizer is usually very pure and typically has a nitrogen content of 46% N. Urea is therefore the fertilizer with the highest concentration of nitrogen, one of the reasons of its popularity.

Urea can be applied as such for straight nitrogenous fertilization, or in combinations with other elements, such as for example NS grades in which nitrogen and sulphur sources are combined, NP (respectively NK) grades in which nitrogen and phosphate (respectively potash) sources are combined, NPK combining the three major nutrients required by the crops, etc.

These different elements can be combined with urea as a physical blend of different products, or products being mixed/processed together into homogeneous granules by e.g. granulation, compaction, etc. Some examples of urea based products:

- NS products such as UAS which are mixtures of urea and ammonium sulphate, for example with a N content of 40% N,
- NPK triple 19 expressed in $N/P_2O_5/K_2O$, which are combinations of urea, DAP (di-ammonium phosphate) and muriate of potash (MOP),
- etc.

Urea and urea based compounds are often blended with other fertilizers in order to adjust the formula and thus supply a balanced nutrition with the different elements required for the plant growth. The main advantages of blending are of course that from a limited amount of available products, it is possible to produce virtually an infinite amount of grades adjusted to the requirement, in a very flexible way. However, blending of urea and of urea based compounds is sometimes difficult or even impossible, due to products chemical incompatibility. Reference is made to the well documented and explicit "Guidance for the compatibility of fertilizer blending materials" published by EFMA in June 2006.

In particular, urea and urea based compounds used in fertilizer are well known to be not blendable with ammonium nitrate and ammonium nitrate based product (CAN, NPK, etc.), as well as with superphosphates (single superphosphate SSP, triple superphosphate TSP, etc.). Urea and urea based compounds are also known to be difficult to blend with calcium nitrate.

These blending incompatibilities or limitations have different causes.

When blending urea based products together with ammonium nitrate based compounds, the mixture will quickly become wet and absorbs moisture from the surrounding, turning the free flowing granules into a wet mud. Even if moisture absorption from the surrounding atmosphere is prevented, the blend will turn wet from its own water content present from the beginning. The reason is that urea and ammonium nitrate form a double salt that is especially hygroscopic. As soon as urea and ammonium nitrate are in contact, this double salt is forming and starts turning liquid. Being more hygroscopic than the initial constituents, it will attract the moisture from the rest of the blend. The formed liquid phase will dissolve the products in contact, thus forming more UAN double salts and enhance the phenomenon that will propagate further.

The incompatibility effect with for example superphosphates and calcium nitrate is different. Many salts contain some water of crystallization, such as superphosphates and calcium nitrate. In presence of such salts, urea has the general tendency to form double salts, thus releasing the water of crystallization. Therefore mixtures of urea and urea based compounds with SSP/TSP and with calcium nitrate will also have the tendency to turn muddy, independently from moisture pick up from the surrounding.

If these products are very dry, then they have the possibility to bind some of the water that would be released from the forming double salts with urea, making the blend still feasible. This is the reason why in the pre-mentioned blending guidance of EFMA, the remark about calcium nitrate and urea is made: the compatibility is limited, moisture pick up must be absolutely avoided, therefore quote: "consider the relative humidity during blending".

It is important to notice that blending UAS with calcium nitrate is much more an issue, due to the formation of UAN (urea ammonium nitrate) and subsequent liquid phase formation. Indeed, ammonium sulphate from UAS can react with calcium nitrate to form ammonium nitrate and calcium sulphate, and ammonium nitrate forms the very hygroscopic UAN double salt with urea as described hereabove.

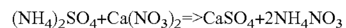

$$(NH_4)_2SO_4+Ca(NO_3)_2 \Rightarrow CaSO_4+2NH_4NO_3$$

In the past, there has been development of a technique allowing blending urea with e.g. TSP. This was based on a sulphur coating of one or both components. Typically urea is coated with about 20% of molten sulphur, in order to create a strong barrier isolating the urea from the superphosphate. The opposite approach was possible, i.e. to produce sulphur-coated TSP in order to make it blendable with urea.

Such an approach suffers significant drawbacks, that the present invention overcomes. First of all such a layer of sulphur, if well tight, creates a delayed release effect since sulphur is insoluble in water. It means that one compound, either urea or TSP depending on which one has been sulphur-coated, will have some delayed release effect which is not necessarily the aim. Moreover, the sulphur shell will remain for very long in the field, having virtually no positive effect for the fertilization. In order to get a proper sulphur-coating, typically 20% of sulphur needs to be applied. If less, the coating is not thick enough and will be imperfect, leading to degradation over time of the blend. This coating act then as a diluent of the fertilizer without bringing extra fertilization value. Moreover, sulphur is incompatible with ammonium nitrate, therefore such sulphur coating technique is anyway not applicable to ammonium nitrate containing blends.

Based on the same principle of an insoluble coating, one can mention the possibilities of blending some polymer-coated urea with e.g. ammonium nitrate. Such polymer-coated urea product is available for example in the North American market, see for example coatings as described in International patent application WO2012/064730. It is produced to get a slow release effect of nitrogen urea. Thanks to this slow release coating, it can be blended with most other products, but by nature its nitrogen will be released with delay compared to the other nutrients. Moreover, such a polymer coating has in itself no fertilizing value and dilutes by several percent the nitrogen content of urea.

FR 2 686 861 describes a coating procedure which substitutes the traditional coating with sealing of the particulated fertilizers by a solid capsule. It provides the fertilizers with a better protection and prevents it more efficiently from caking than a traditional coating does. The coating procedure is carried out by spraying the particulated fertilizers with a first reagent in the form of a mineral base, such as magnesium, calcium or barium oxide, followed by an aqueous solution of a second reagent, such as phosphoric, sulphuric, nitric or citric acid which reacts with the first reagent to form a solid capsule of a metal salt. The application of the base and the acid has to be repeated twice to form the solid capsule. According to this patent the contact between the acid and the granule is avoided to prevent the acid to form a slurry with the granule. Such a coating would not adhere sufficiently to the fertilizer core and would not be suitable in blends Goodale et al. (U.S. Pat. No. 3,419,379) shows a coating for ammonium nitrate (NH4NO3) granules in which the granules were first coated with an acidic super phosphoric acid (H3PO4) or oleum. The wet granules were then contacted with basic materials such as NH3, MgO, or CaO. The reaction product of the acid with the basic material produced a coating around the granules which prevented them from caking and retarded their dissolution on contact with moist soil.

WO99/15480 relates to a method for coating particulated fertilizers like complex nitrogen-, phosphorus- and potassium fertilizer (NPK), nitrogen- and potassium type fertilizer (NK), ammonium nitrate fertilizer (AN), calcium nitrate fertilizer (CN) or urea to reduce dust formation and caking during handling and storage. There is no reference to any physical blends. The method comprises applying an aqueous solution of a mineral acid, such as phosphoric acid, sulphuric acid, nitric acid or citric acid and a mineral base, such as magnesium oxide, calcium oxide, barium oxide, dolomite or a mixture of two or more. Said combined treatment is performed only once to form a nutrient containing shell of a metal salt or mixture of metal salts on the particulate fertilizer. The ratio between said acid and said base applied onto the particulated fertilizers is between 1.0 to 1.5 weight/weight. Such a process would not result in a coating suitable for making fertilizer blends.

The present invention overcomes these different drawbacks such as delayed release or dilution of the nutrient content without bringing fertilizing properties. Moreover it is cheap to implement and especially adapted to blenders.

OBJECT OF THE INVENTION

It is the object of this invention to overcome the chemical blending incompatibilities of urea and urea-based compounds and make urea universally blendable. Another object of the invention is to find a method of producing passivated urea and urea based compounds. A third object is to obtain a blend of passivated urea and ammonium nitrate. A further object is to obtain safe ammonium nitrate fertilizer blend.

SUMMARY OF THE INVENTION

The objects of the invention are obtained by the product and method described in the following and as defined by the appended claims.

DETAILED DESCRIPTION OF THE INVENTION

The invention concerns a method of producing passivated urea or urea based compounds for fertilizer blends wherein the urea particles are treated with a mineral acid that reacts with urea and creates a grasping layer. A solid base in powder form is thereafter added in excess to the particles to coat the acidified particle surface. The term "passivation" is used to express that the blending incompatibility of urea with different compounds is a phenomenon that happens at the surface of the particles, on the contact points. The surface of urea is in general active, as surface reactions can occur with other compounds. Our treatment makes the urea surface inactive, i.e. passive, therefore the term passivation. The unwanted reactions are blocked thanks to this passivation. The term passivation is also chosen to insist on the fact that this invention is not just a "coating" or simply building a layer of a third compound, such as applying a thick coating of for example sulphur or a polymer. It is really about performing surface reactions; first acid with urea as a grasping layer and then acid with base.

The particles are preferably treated with 0.1 to 2.0 weight % acid and 2 to 6 weight % base. A further acid treatment is preferred. The mineral acid may be selected from sulphuric acid, phosphoric acid or nitric acid, and the solid base is selected from MgO, dolomite, magnesite, limestone, calcite, chalk, calcium oxide or calcium hydroxide. Other preferred treatments include 0.2 weight % acid and 3-5.5 weight % base and 0.9 to 1.0 weight % acid and 2.5 to 4.0 weight % solid base, based on the weight of the urea particles. The urea based compounds are selected from urea, UAS, NPK, NK, NP and urea with micronutrients. The urea could be pre treated by drying or preheating. Post treatment by coating is also possible.

The invention also concerns a fertilizer blend comprising the passivated urea or urea based compounds with one or more of AN or AN-based compound, NS products, superphosphates, and more generally with a priori most compounds that urea is susceptible to react with when in direct contact. Preferably the blend comprises urea or urea based compounds and ammonium nitrate based compounds. The ammonium nitrate compounds would contain salts able to bind crystallization water, when necessary. The salt is selected from magnesium nitrate or magnesium sulphate or mixtures thereof. Preferably the amount of salt is 0.5 to 3 weight %. A preferred blend comprises passivated urea and ammonium nitrate with magnesium nitrate. A safe blend comprises more than 40 weight % of the passivated urea.

Thanks to a passivation process of the urea particles they are turned into a new product of passivated urea. The surface of the urea particles is treated with a small amount of mineral acid, such as sulphuric acid or phosphoric acid, which has the property to react with the urea. Then a solid base in powder form, such as magnesium oxide or dolomite, is added in excess to coat the acidified surface, and reacts with the acid. The final layer will passivate the urea surface thanks to a combination of 1) a grasping layer made of double salts of urea, 2) metal salts and 3) unreacted base.

Variations of this principle are possible, but one key aspect is clearly to add a sufficient amount of acid first in order to create a grasping layer. If acid is added after the powder, then the passivation layer is weak, because it does not adhere sufficiently, and a large part of the powder is actually not fixed but lost.

As urea and ammonium nitrate are the most difficult products to put together in a blend, primary focus was put on obtaining proper blends of these two compounds, then to extend the work to other applications such as calcium nitrate and superphosphates. The description is based on making possible such "impossible" blends, but not limited to. Indeed the technique and new product developed according to this invention are applicable to other fields/other mixtures etc.

The invention also concerns passivated particles of urea or urea based compounds having a surface comprising double salts of urea, metal salts and unreacted base obtainable by treating the particles with a mineral acid that reacts with urea and an excess of a solid base in powder form.

Process

The core of the process is to use a system where synthesis of the passivation layer can be performed with sufficient homogeneity. Typically a coating drum, or a rotating blender, or a pan, i.e. standard techniques used in the fertilizer industry. A cement truck, with its rotating section, can be perfect for the purpose, used as mobile blending unit. In the rest of the text, the term "drum" is indifferently used for this section of the process, but not limited to. For example all tests performed to develop this invention were actually performed at a small scale, using a concrete mixer of about 50 L.

Pre-treatment and post-treatment before and after the drum can be used, depending on the actual conditions, quality of materials available, targeted quality of the final product, etc.

For example if the passivated urea is to be transported/stored after the passivation, addition of water-repellent coating can be of interest, to maintain the quality of the product until its final use. Addition of such a coating is a standard process step in fertilizer industry. It is as such not core of this invention but brings further quality to the product.

The production process can be performed as a batch process, or continuously.

Batch Process:

For a batch process the different compounds would typically be introduced one by one, in a sequence such as:

- urea
- then acid
- then alkaline powder
- then extra acid if necessary
- then coating if necessary
- then second compound such as ammonium nitrate, TSP, etc Continuous Process:

Urea (or urea based compound) is introduced into a coating drum, preferably after pre treatment. The acid is added, thereafter the alkaline powder and then extra acid, if necessary. Pre-treatment is as such not necessary but can help. Pre-treatment is typically drying and pre-heating. It can be performed with e.g. a cross-flow exchanger such as a fluidized bed equipment, a co-current or counter current heater/dryer, or e.g. a bulk flow heater, etc. Pre-treatment can especially be of interest to flatten fluctuations of quality of the products that are used, for example in case they may have suffered from moisture pick up between the time they have been produced and the time they are used to produce the blend. Moreover, if the products are warmer than the ambient temperature, it limits the pick of moisture during the handling.

Post-treatment can also be performed. A dedusting step is of course an important plus to improve the product quality but is as such not a must. If the product is not dedusted, loose dust will simply have a tendency to accumulate at the bottom of the bag in which the product would be stored. Drying is also a plus, and can be combined with a dedusting step. During most trials, drying was not performed proving that it is not as such required, but of course removal of water is always a benefit to ensure higher storage properties of the product.

Drying is of specific interest especially not only to remove water from the raw materials or absorbed during the processing, but also because the reaction of the acid with the alkaline powder does produce water. Just to illustrate with an example:

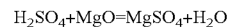

$$H_2SO_4+MgO=MgSO_4+H_2O$$

If a dedusting step is performed, typically by the use of air, then this air is cleaned with standard techniques, preferably using dry techniques such as cyclones, electrofilters or bag filters for example, allowing a direct recycling of the dust back to the drum for reprocessing. In case of wet scrubbing for example, then process integration with e.g. NPK plant can be optimized, or production of a liquid fertilizer using the scrubbing liquor.

The particles can optionally be coated by a standard coating, before they are blended with other compounds in a final step.

Screening to calibrate the product and remove fines/oversize/lumps due to e.g. progressive scaling of the equipment, can also naturally be performed either as pre or post treatment or both.

Testing

It was first studied/observed that the blending of standard quality urea granules together with standard quality ammonium nitrate or CAN was sometimes possible, provided that the product was dry from the beginning, bagged to avoid any moisture pick up, and stored at ambient temperature. To simulate tougher conditions, a specific laboratory test was developed. In particular higher temperatures typically encountered locally due to sun radiations when the bags are stored outside or even in some warehouses, where the temperature can rise significantly. A generally accepted temperature to simulate such storage conditions is 50 degrees C., that is typically used when performing e.g. safety tests on the thermocycling of AN products.

Therefore, to evaluate the performance of the products tested during the development of this invention, a so-called jar test was implemented. The jar test is as follow: in a glass container of 1000 mL, 150 g of urea based compound in a granular form is blended with an equivalent amount of the other compound, e.g. ammonium nitrate granules, sealed hermetically and stored during 24 hours at 50 degrees C. Since the recipient is in glass, it is easy to observe the behaviour and the evolution of the product inside. This test is stringent, since the product has to withstand for 24 hours a temperature that is rarely reached under most climates, and especially for such a long period of time.

Results from the Jar Test are Simple:

- When the products are well blendable, they keep their aspect, remaining nicely free flowing.
- On the opposite, when products are not blendable, such as urea with ammonium nitrate, then a large amount of liquid phase is generated, and remaining undissolved granules are visible within this liquid phase. When the temperature is cooling down, the whole crystallizes together.
- In between, different situations exist: for example some few granules get half agglomerated half molten together (typically if e.g. one urea granule was present without being passivated as per invention), i.e. a local phenomenon not influencing the rest. Or a global phenomenon, when e.g. the granules are getting sticky and muddy.

Second phase of the development was performed at a pilot scale per batch process, using a concrete mixer of ~50 L volume for both passivation and coating when needed, and a small fluidized bed cooler of 1 $m^2$ for dedusting. The invention will be further illustrated by the following examples: All solid blends of two compounds described in the examples below were performed on a 50/50 basis, expressed in mass. AN (ammonium nitrate) was AN33,5 stabilized with magnesium nitrate, except specified otherwise.

EXAMPLE 1

Standard products were mixed together in a jar and exposed to a step by step temperature increase.

Two blends were prepared in the jar test, the first was urea granules blended with CAN stabilized with aluminium sulphate and the second CAN stabilized with magnesium nitrate.

After being exposed to 30 degrees C. for 24 hours, both blends remained correct. At 40 degrees C., the blend with CAN stabilized with aluminium sulphate started to turn wet and liquefy, while the other one remained in perfect state. At 50 degrees C., both blends turned totally into slurries.

EXAMPLE 2

In the laboratory, urea granules were submerged into a beaker full of concentrated sulphuric acid (96% wt) at ambient temperature and stirred for 10 to 20 seconds to ensure a good contact of the urea surface and the acid without dissolving the granules into the liquid.

Granules were then extracted and placed on a Büchner filter for a first removal of the excess of acid, whereafter paper was used to further dry the samples until a constant weight was reached. The acidified granules had a pH of 2.6. The amount of ammonium ions, NH4+, was checked and found to be 40 ppm only, indicating that no urea was decomposed during the treatment, that would have shown presence of ammonium ions (in the form of ammonium sulphate).

The surface of these granules was then treated with magnesium oxide powder, excess magnesium oxide powder being removed by sieving. In that way the pH of the acidified granules was raised from 2.6 to more than 10. The chemical analysis of the product indicates that it contained 0.85% sulphuric acid equivalent and 2,8% magnesium oxide equivalent.

The resultant product was blended with AN, and passed successfully the jar test. Variations of the previous tests were performed, using respectively phosphoric acid (fertilizer grade, 54% $P_2O_5$) and magnesium oxide, but also sulphuric acid with dolomite, and leading to similar successful results. Further tests were then performed at larger scale, using sulphuric acid and magnesium oxide as reference.

EXAMPLE 3

In a concrete mixer of about 50 l volume, 20 kg of urea granules were placed. A target amount of sulphuric acid was dropped onto the rolling granules, which requires about 5 minutes. The product was then rotated further for 5 minutes in order to promote a good uniform acid distribution. A target amount of magnesium oxide powder was added using a small vibrating feeder, and the product was rotated for another 5 minutes to get a uniform spreading of the powder, well visible on the white surface of the urea granules. Part of the product could be sampled as such, and part was further dedusted in a fluidized bed cooler for 4 minutes. Air in the fluidized bed cooler is dry (dew point of 5 degrees C.) and warm (35 degrees C.), to dedust the product. No drying effect, or very minor, was observed in the fluidized bed under such conditions.

The amount of respectively equivalent acid and equivalent magnesium oxide in the final product was checked. The amount of acid was always very close to the dosed amount, but the amount of powder was ranging from 60 to 90% of the dosed amount. All the figures mentioned in the examples correspond to the dosed amounts, except specified otherwise.

EXAMPLE 4

Following this procedure for concrete mixture testing, different mixtures were tested:

1% sulphuric acid with 2% of magnesium oxide. The product failed in the jar test.

1% sulphuric acid with 4% of magnesium oxide. The product passed successfully the jar test.

0.5% sulphuric acid with 4% of magnesium oxide. The product failed in the jar test.

0.5% sulphuric acid with 6% of magnesium oxide. The product passed successfully the jar test.

0.2% sulphuric acid with 4% of magnesium oxide. The product nearly passed the jar test.

0.2% sulphuric acid with 6% of magnesium oxide. The product passed the jar test.

EXAMPLE 5

Alternative tests were performed to fine tune the technique.

6% of powder was added first, and thereafter 0.2% of acid. The product was analysed and contained only 2.3% of powder and 0,15% of acid. The product failed in the jar test. It is however remarkable that most acid could be analysed on the granules. The yield of powder fixation was however very low.

4% of powder was added first, and therafter 1% of acid. The product failed however in the jar test.

Acid was tested in a split application: 0.5% sulphuric acid first, then 4% magnesium oxide, then 0.5% again. The product passed the jar test.

These example show clearly that a first addition of acid is necessary, to act as a grasping layer for the powder but also to perform a uniform passivation of the surface, mandatory for proper blending with ammonium nitrate.

Post-application, e.g. of acid, is of course possible and can be part of production adjustments in an industrial unit.

EXAMPLE 6

Tests were performed to evaluate the dustiness of the products.

Dustiness is defined in ppm as the amount of weight loss after fluidizing the product in a standardized procedure for 2 minutes. Figures below 300 ppm lead to a virtually non-dusty product during handling, while products with more than 1000 ppm will be dusty during handling. Standard urea granules typically range between 100 and 1000 ppm of dustiness level by this technique.

Before dedusting step in the pilot plant, i.e. product sampled just after the concrete mixer, figures were high ranging from 2500 to 10000 ppm if using 0.2% acid only. The highest figures are due to small lumps of dust that totally disintegrate in the dust test. When using 1% of acid, figures were as well in the range 2000-3000 ppm. Lowest figures before any dedusting were obtained with pre and post addition of acid. Tests with 0.5% of acid, then 4% of powder, then 0.5% of acid, gave figures of 1000 ppm.

After the dedusting step in the pilot plant, figures were typically 800 to 1200 ppm dust if using 0.2% acid only versus less than 500 ppm when 1% of acid was used. Moreover, after addition of a coating oil as it is standard in fertilizer industry, the dustiness could be further reduced. In any case, coating of the product with a water-repellent coating is advisable to limit any moisture pick up and moisture transfer during handling prior and after blending.

From those tests, it shows that adding acid in two steps can be a good way to limit the dustiness of the product, which is of special interest for a batch process. However, if a dedusting step is foreseen in the process, there were no differences between products where 1% of acid was directly added or when it was added in two times 0.5%.

EXAMPLE 7

Moisture Transfer:

All urea passivated in the concrete mixer got a significant moisture increase during the test, in particular due to the hygroscopicity of the concentrated sulphuric acid.

The moisture train was analysed by Karl Fisher method: Urea before any treatment 0.36% water.

Urea sampled in the concrete mixer after addition of sulphuric acid 96%: 0.58% water, due to moisture pick up from the surrounding environment.

Urea sampled after addition of 4% MgO: 0.72% water (since the reaction between sulphuric acid and magnesium oxide release 1 mol of water).

Urea sampled after the fluidized bed dust removal (4 minutes at 35 degC): 0.7% water.

Final sample, kept at 50 degrees C. over the week end: 0.6% water. Urea sampled after the fluidized bed dust removal (4minutes at 65 degrees C.): 0.54% water.

Final sample, dried by infrared at 100 degrees C. : 0.16% water.

This moisture train shows that most water can be easily removed in an industrial process. First of all by preventing moisture pick up during the application of the acid, second by including a drying step at gentle temperature in the process, typically between 50 and 100 degrees C.

In any case, despite the relatively high water content of the samples produced in our testing, the tests with AN were successful as described above. To be dryer means only to build extra robustness in the product.

EXAMPLE 8

In order to evaluate the moisture transfer potential from such passivated urea into the AN during the blend, a sample of 20 g of passivated urea was placed in a cup in a dessicator filled with 200 grams of AN, and kept overnight.

If it was kept at ambient temperature, the water content of the passivated urea decreased from 0.68% down to 0.52%. If it was kept at 50 degrees C., the water content of the passivated urea decreased from 0.68% down to 0,46%.

It is therefore crucial that either the AN compound has some water binding capacity, or that the passivated urea is sufficiently dry. This can be done either to prevent any moisture pick up during its production and even better, to include a drying step. In our tests, the AN 33.5 was stabilized with 2.3% magnesium nitrate and contain typically ~0.5-0.8% before blending. The test failed if the AN contained 1.3% of water from the start, which correspond to the limit of no free water at 50 degrees C.

EXAMPLE 9

Some extra tests were performed to check the potential of the invention for other blends.

Urea was blended with TSP granules containing 1% of water analysed by Karl Fisher (KF). The blend could not pass the jar test.

Urea passivated with 1% acid and 4% magnesium oxide was blended with the same TSP. It passed successfully the jar test.

UAS was passivated with 1% of sulphuric acid and 4% of magnesium oxide, and blended with calcium nitrate granules. The blend passed the jar test.

In this invention we are working with low ratios acid to base. As demonstrated by the examples, this passivation process is not working with a constant, nor fixed ratio of acid to base. The less acid that is added, the more base is required to compensate. A large excess of base is used.

The invention claimed is:

1. A method of producing passivated particles comprising urea, or urea-based compounds, for fertilizer blends, said method comprising:

treating urea containing particles with 0.1 to 2.0 weight % of a mineral acid that reacts with urea, so as to create an acidified particle surface and form a grasping layer made of a double salt of urea; and thereafter adding an excess, 2 to 6 weight %, based on the weight of the urea-containing particles, of a solid base in powder form to the particles so as to coat the acidified particle surface and obtain a layer comprising 1) said grasping layer, 2) metal salts formed from reacting said mineral acid with said solid base in powder form, and 3) unreacted base.

2. The method according to claim 1, wherein the urea-containing particles are treated with 0.9 to 1.0 weight % acid and 2.5 to 4.0 weight % solid base, based on the weight of the urea-containing particles.

3. The method according to claim 1, wherein the urea-containing particles are treated with 0.2 to 0.8 weight % acid and 3-5.8 weight % base, based on the weight of the urea-containing particles.

4. The method according to claim 1, wherein a further acid treatment step is performed.

5. The method according to claim 1, wherein the mineral acid is sulphuric acid, phosphoric acid or nitric acid.

6. The method according to claim 1, wherein the solid base is MgO, dolomite, magnesite, calcite, calcium oxide or calcium hydroxide limestone, or chalk.

7. The method according to claim 1, wherein the urea based compound of the urea-containing particles is urea, UAS, NPK, NK, NP, urea with micronutrients, or any mixture thereof.

8. The method according to claim 1, wherein the urea-containing particles are pretreated by drying or preheating.

9. The method according to claim 1, wherein the passivated urea-containing particles are further coated.

10. A fertilizer blend comprising:

passivated particles comprising urea, or a urea-based compound, produced by the method according to claim 1, and one or more of ammonium nitrate, an ammonium nitrate-based compound, calcium nitrate, superphosphates, NS products, or a compound which urea is susceptible to react with when in direct contact.

11. The fertilizer blend according to claim 10, comprising passivated particles comprising urea, or a urea-based compound, and ammonium nitrate-based compounds, and optionally salts able to bind crystallization water.

12. The fertilizer blend according to claim 11, wherein the salt is magnesium nitrate, magnesium sulphate or a mixture thereof.

13. The fertilizer blend according to claim 11, wherein the amount of salt is 0.5 to 3 weight %.

14. The fertilizer blend according to claim 11, comprising passivated particles comprising urea, or a urea-based compound, and ammonium nitrate comprising magnesium nitrate.

15. The fertilizer blend according to claim 10, comprising more than 40 weight % of passivated particles comprising urea, or urea-based compound.

16. Passivated particles of urea or urea-based compounds, having a surface comprising 1) a grasping layer of double salts of urea, 2) metal salts and 3) unreacted base, wherein the passivated particles of urea or urea-based compounds are obtained by treating urea-containing particles with 0.1 to 2.0 weight % of a mineral acid that reacts with urea, and an excess, 2 to 6 weight %, of a solid base in powder form, based on the weight of the urea-containing particles.

* * * * *